United States Patent [19]

Hansen

[11] 4,424,035
[45] Jan. 3, 1984

[54] SELF-CENTERING DENTAL FACE-BOW
[76] Inventor: Gorm P. Hansen, 1501 SE. 23rd Ave., Pompano Beach, Fla. 33062
[21] Appl. No.: 310,411
[22] Filed: Oct. 9, 1981
[51] Int. Cl.³ .............................................. A61C 19/04
[52] U.S. Cl. ....................................................... 433/73
[58] Field of Search ........................ 433/72, 73, 68, 69; 33/174 D

[56] References Cited
U.S. PATENT DOCUMENTS

| | | | |
|---|---|---|---|
| 1,052,806 | 2/1913 | Evans | 433/73 |
| 3,024,534 | 3/1962 | Wilkinson | 433/73 |
| 3,336,670 | 8/1967 | Heydenreich | 433/73 |
| 4,261,696 | 4/1981 | Hobo | 433/73 |
| 4,330,277 | 5/1982 | Beu | 433/73 |

FOREIGN PATENT DOCUMENTS 348620  2/1922  Fed. Rep. of Germany ........ 433/72

Primary Examiner—John J. Wilson
Attorney, Agent, or Firm—Diller, Ramik & Wight

[57] ABSTRACT

A self-centering dental face-bow comprising an elongate cross-bar which is adapted to be disposed across the front of a dental patient's face in spaced relationship thereto, a pair of arms extending transversely from the cross-bar in order to present each in spaced relationship along an associated side of a patient's face, a pair of hinge pointers of which each extends transversely from one of the arms toward the other arm to engage an associated side of the patient's face, a mount which is generally centrally disposed on the cross-bar and is adapted to carry various dental appliances which are to be engaged by a patient's mouth, and the arms are movable equidistantly in relation to the mount toward and away from each other in the direction of length of the cross-bar.

5 Claims, 3 Drawing Figures

SELF-CENTERING DENTAL FACE-BOW

BACKGROUND OF THE INVENTION

In the dentistry field it is conventional for a dentist to obtain impressions of a patient's dental structure in order to diagnose the patient's needs. Normally, these impressions are taken by having a patient bite down on a bite-fork which contains a molding medium in order to leave an exact impression of the patient's teeth in the molding medium. The dentist then subsequently makes a cast of the dental patient's teeth from the impression molded onto the bite-fork.

However, in order properly to diagnose a patient's dental needs, a dentist must be able to ascertain the location of the patient's teeth in relation to his jaw and jaw hinge axis. In order to obtain this relative location of the patient's teeth, it has been conventional to mount the impression tray and bite-fork or the like on a face-bow. Ordinarily, a face-bow comprises an arcuate member which bridges across the front of a patient's face from one side thereof to the other, a universal connector or mount which is generally centrally located on the arcuate member and is adapted to receive the bite-fork or impression tray or the like, to be engaged by the patient's teeth, and a pair of hinge pointers each of which extends inwardly from one of the sides of the arcuate member to engage the sides of a patient's face in axial alignment with the patient's jaw hinge axis. These hinge pointers, which are disposed in coaxial alignment with the patient's jaw hinge axis, are then used to establish a line of reference from which the dentist can determine the teeth locations in relation to the patient's jaw hinge axis. The dentist then ascertains the location of the patient's teeth by measuring the relative distances between the bite-fork and the patient's jaw hinge axis, as defined by the coaxially disposed hinge pointers, and the distance between the center of the patient's dental pattern in relation to the centrally disposed mount on the cross-bar.

However, this procedure is normally quite arduous for the adjustment of the width (the distance between the hinge pointers) of the conventionally used face-bows entails an independent adjustment of the projection of each hinge pointer towards its associated side of a patient's face. In other words, the dentist must maintain the universal connector or the like, which is adapted to receive the impression tray or bite-fork or the like, in general central disposition in relation to the hinge pointers, and then adjust the hinge pointers inwardly to engage the patient's face over the center of his jaw hinge condyles. Therefore, in order to adjust the face-bow to a patient's face, the dentist must be aided by an assistant because one person is needed to hold the bite-fork in a central position relative to the patient's face, and another person is required to adjust each of the hinge pins to engage a patient's face. Obviously, in order to maintain the bite-fork in central position relative to the patient's face, each of the hinge pointers must be moved equidistantly toward the patient's face, or the universal mount must be moved one way or the other in order to compensate for any unequal projection of one hinge pointer in relation to the other. In any event, the dentist and his assistant must delicately adjust the hinge pointers and/or the universal connector, often in a trial-and-error manner, in order eventually to obtain the location of the patient's dental structure.

BRIEF SUMMARY OF THE INVENTION

The present invention pertains to a self-centering face-bow which alloys a dentist to move both the hinge pointers thereof simultaneously and equidistantly relative to the centrally disposed mount or universal connector in order to adjust the width of the face-bow. In order to place the face-bow of the present invention on a patient's face and to adjust it for the patient's face, the dentist merely has to place one of the hinge pointers in alignment with the patient's jaw hinge axis and then manipulate the adjusting means of the present invention in order to draw the hinge pointers simultaneously inwardly toward each other until both engage the patient's face. Having so adjusted the face-bow in this manner, the dentist is assured that the bite-fork and universal connector or the like are centrally disposed between the hinge pointers. This, of course, absolves the dentist of any need for mathematical computations or the like, in order to center this universal connector in relation to the hinge pointers. Also, due to the simultaneous movement of both the hinge pointers, the dentist can place the face-bow on the patient's face without the aid of an assistant as he can hold the face-bow with one hand and adjust its width with the other.

DETAILED DESCRIPTION

Figure 1:
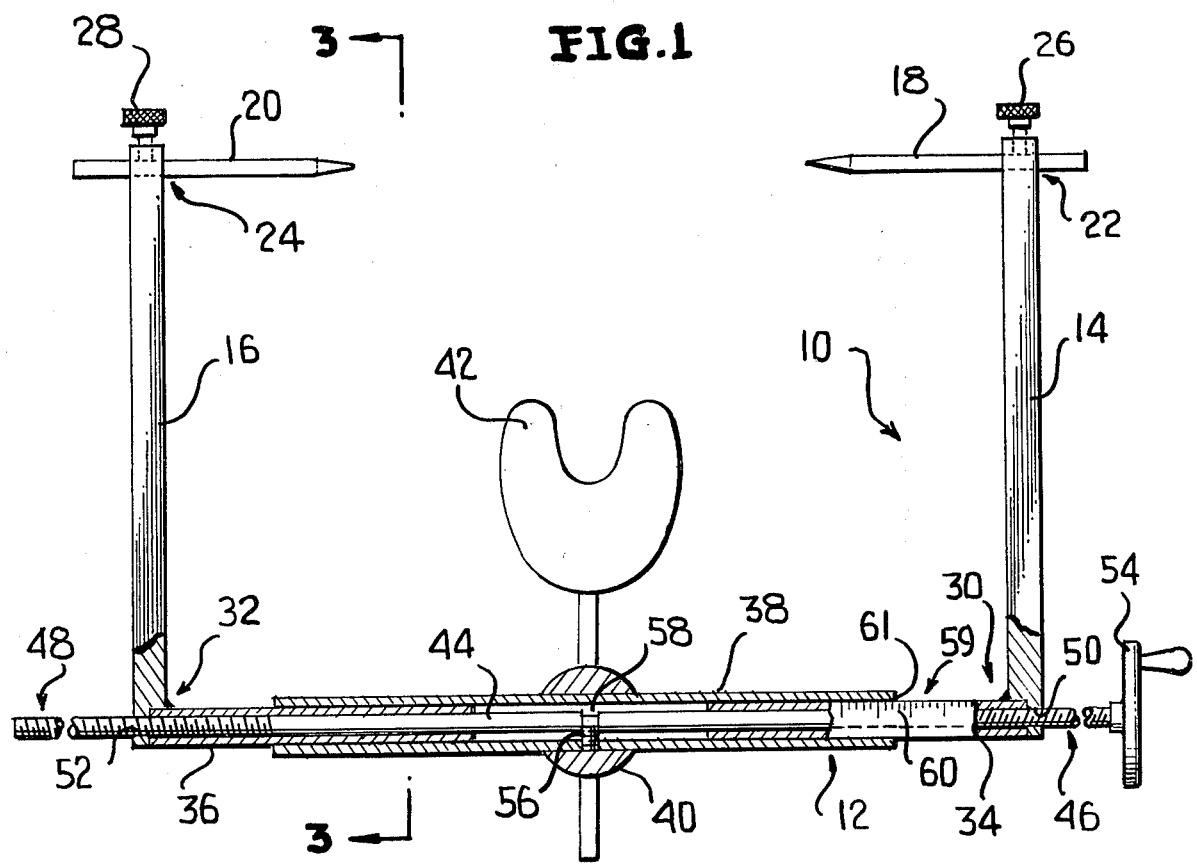
FIG. 1 is a top plan view partly in cross section of a preferred embodiment of the face-bow of the present invention.

Referring to FIG. 1, a face-bow of the present invention is generally designated by the reference character 10. The face-bow 10 comprises an elongate cross-bar 12 which is adapted to extend across the front of a patient's face in spaced relationship thereto, a pair of identical arms 14, 16 each of which is adapted to extend generally transversely from the cross-bar 12 along an associated side of the patient's face in spaced relationship thereto, and a pair of hinge pointers 18, 20 which extend generally transversely from the arms 14, 16 respectively, to engage associated sides of the patient's head. More particularly, each of the hinge pointers 18, 20 is adapted to extend transversely through one end portion or a first end portion 22, 24 of its associated arm 14, 16, respectively, and is secured thereto by means of a set screw 26, 28 or any other suitable means, as is conventional. At an opposite end portion or a second end portion 30, 32 of each of the arms 14, 16 respectively, there is disposed a tubular member or a first tube 34, 36 which extends transversely inwardly therefrom toward the other first tube of the other arm. The first tubes 34, 36 are disposed in coaxial spaced opposing relationship and a second tube 38 of the cross-bar 12 extends coaxially in external telescopic relationship therewith. Each of the first tubes 34, 36 has external dimensions of predetermined value and the second tube 38 has internal dimensions which are slightly greater than the predetermined external dimensions of the first tube 34, 36. This allows axial telescopic movement of the first tubes 34, 36 relative to the second tube 38 thereby to allow the arms 14, 16 and their respective hinge pointers 18, 20 carried thereon to be moved toward and away from each other in the direction of length of the cross-bar 12.

The cross-bar is provided with a mount, universal connector, or mounting means 40 disposed generally centrally thereon which is adapted to receive various dental appliances which are to be engaged by the patient's mouth, as, for example, a bite-fork, impression tray or the like 42. The cross-bar 12 also has adjusting means or a threaded rotatable rod or shaft incorporated therewith which allows the arms 14, 16 and the hinge pointers 18, 20 carried thereon to be moved toward and away from each other simultaneously and equidistantly relative to the mounting means 40. The rod 44 extends coaxially through the first tubes 34, 36 and the second tube 38 and is provided at opposite ends 46, 48 respectively, with screw threads (unnumbered) which are adapted to engage threaded nuts 50, 52 disposed in each of the first tubes 34, 36 respectively. The screw thread at the end portion 46 of the shaft 44 has an opposite-handed direction to that disposed at the end portion 48 thereof. The rotatable shaft 44 also includes a hand wheel 54 at one end thereof, for example, end 46 which is adapted to be manipulated by the dentist in order to rotate same and thereby cause the arms 14, 16 to move equidistantly and in opposite directions relative to each other. In order to preclude axial movement of the rotatable shaft 44 relative to the second tube 38, the second tube is provided with a tang 56 which extends radially inwardly from an interior wall thereof to engage a generally centrally disposed circumferential indentation 58 of the shaft 44.

Figure 3:
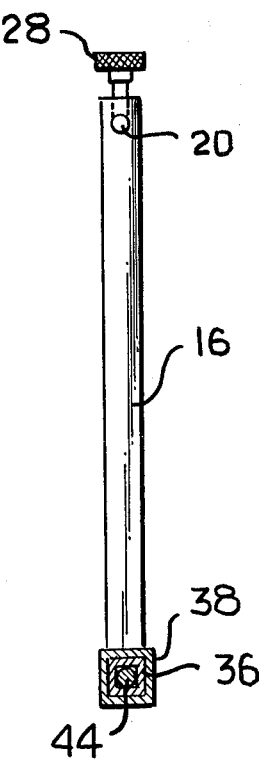
FIG. 3 is a sectional view of a portion of the face-bow of the present invention taken along line 3—3 of FIG. 1.

The face-bow 10, of the present invention further includes cooperative means which preclude relative rotation between the first tubes 34, 36 and the second tube 38. In a preferred embodiment of the invention, the cooperative means is defined by the first tubes 34, 36 and the second tube 38 which have a non-circular cross section, and in particular have a rectangular cross section. This feature of the invention is most clearly shown in FIG. 3 wherein the first tube 36 of the arm 16 is illustrated as having a rectangular cross section which prevents it from rotating relative to the second tube 38 which likewise has a rectangular cross section.

Figure 2:
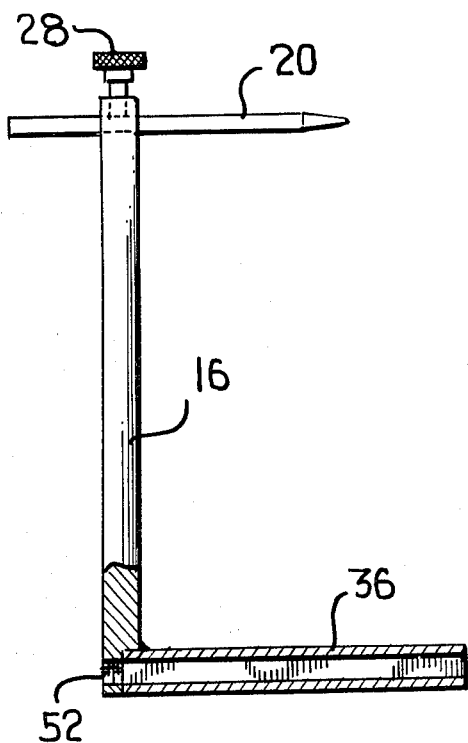
FIG. 2 is a plan view partially in cross-section of a portion of the face-bow of the present invention.

FIG. 2 is an illustration of one of the arms of the face-bow 10, for example, arm 16 and its associated first tube 36. From this figure, it will be noted that the tube 36 extends generally transversely from the arm 16 and its associated first tube 36. From this figure it will be noted that the tube 36 extends generally transversely from the arm 16 and is welded or otherwise suitably secured thereto. Likewise, in the preferred embodiment of the invention, the threaded nut 52 is welded or otherwise secured to the interior walls of the first tube 36. This very same construction is, of course, to be utilized relative to the arm 14 and its associated first tube 34 and threaded nut 50.

The face-bow 10, of the present invention, further includes gauge means 59 which allow the dentist to ascertain a measurement of the distance between the hinge pointers 18. This gauge means 59 is defined by a plurality of marks 60 inscribed or otherwise disposed on one of the first tubes, for example, the first tube 34, which are adapted to be viewed in registry with one of the ends of the second tube 38, for example, the end 61 (FIG. 1).

By using the face-bow 10 of the present invention, a dentist can be spared much of the tedium extant in the conventional procedure for obtaining casts of a patient's dental structure. It is also believed that the dentist will be able to preform this procedure unassisted because he merely has to take the face-bow 10 in one hand and place the bite-fork 42 or the like in the patient's mouth, and then rotate the hand wheel 54 to adjust the width of the face-bow until the hinge pointers 18, 20 engage their associated sides of the patient's face in substantial alignment with his jaw hinge axis. In this manner, a dentist can adjust the width of the face-bow 10 to mount same on a patient's head without having to proceed in the trial-and-error manner of adjusting each of the hinge pointers 18, 20 independently of the other, as is conventional.

It is to be noted that the descriptions and illustrations disclosed herein are of the preferred embodiments of the present invention and are not intended to limit the scope and spirit of this invention any further than is required by the appended claims.

I claim:

1. A self-centering dental face-bow comprising in combination an elongated cross-bar adapted to be disposed across the front of a dental patient's face in spaced relationship therewith, a mount which is adapted to receive various dental appliances which are to be engaged by a patient's mouth, said mount being disposed generally centrally on said cross-bar, a pair of spaced arms extending transversely from said cross-bar for disposition along associated sides of a patient's head in spaced relationship therewith and being movable toward and away from each other in the direction of length of said cross-bar, means disposed on each of said arms for engaging an associated side of a patient's head, means incorporated with said cross-bar for adjustably moving said arms toward and away from each other equidistantly in relation to said mount thereby to adjust the spacing between said arms and maintain said mount in said generally central disposition, said cross-bar being a tube, each of said arms including a tubular portion extending coaxially with said cross-bar tube, said tubular portions being slidably received within an associated end of said cross-bar tube, said adjustably moving means including a rotatable shaft extending coaxially through said cross-bar tube and said tubular portions and being relatively rotatable thereto, said shaft having right hand threads at one end thereof for threadingly engaging one of said arms and left hand threads at another end thereof for threadingly engaging the other of said arms, whereby upon rotation of said shaft said tubular portions of said arms move slidably toward and away from each other, said cross-bar and shaft include cooperative means for precluding axial movement of said shaft relative to said cross-bar and, said cooperative means includes an inwardly directed tang disposed generally centrally within said cross-bar which relatively rotatably engages a circumferential indentation disposed generally centrally on said shaft.

2. The face-bow as defined in claim 1 including gauge means for indicating the relative distance between said engaging means of said arms.

3. The face-bow as defined in claim 2 wherein said gauge means comprises a plurality of marks inscribed on said tubular portion of one of said arms which are adapted to be registered with the end of said cross-bar associated with said arm.

4. The face-bow as defined in claim 3 wherein said means for engaging comprises a hinge pointer extending transversely from each of said arms toward said associated side of a patient's head.

5. The face-bow as defined in claim 4 wherein each of said hinge pointers extends through its associated arm and is secured thereto by a set-screw thereby to adjust the transverse extent of said hinge pointers.

* * * * *